United States Patent [19]

Choy et al.

[11] Patent Number: 4,902,273
[45] Date of Patent: Feb. 20, 1990

[54] HEART ASSIST DEVICE

[76] Inventors: Daniel S. J. Choy, 892 Riverbank Rd., Stamford, Conn. 06903; Robert B. Case, 130 E. 75th St., New York, N.Y. 10021

[21] Appl. No.: 171,807

[22] Filed: Mar. 22, 1988

Related U.S. Application Data

[60] Division of Ser. No. 809,164, Dec. 16, 1985, Pat. No. 4,771,765, which is a continuation-in-part of Ser. No. 582,118, Feb. 21, 1984, Pat. No. 4,685,446.

[51] Int. Cl.$^4$ .............................................. A61B 19/00
[52] U.S. Cl. .................................... 600/18; 604/101; 623/3
[58] Field of Search ........................... 600/16, 17, 18; 604/96–99, 101, 270; 128/344; 623/3

[56] References Cited

U.S. PATENT DOCUMENTS

| | | | |
|---|---|---|---|
| 2,489,067 | 11/1949 | Wild | 604/270 |
| 3,266,487 | 8/1966 | Watkins et al. | 600/18 |
| 3,592,183 | 1/1971 | Watkins et al. | 600/18 |
| 3,720,199 | 3/1973 | Rishton et al. | 600/18 |
| 4,154,227 | 5/1979 | Krause et al. | 600/18 |
| 4,256,622 | 1/1981 | Hutchins, IV | 600/18 |
| 4,261,339 | 4/1981 | Hanson et al. | 600/18 |
| 4,439,186 | 3/1984 | Kuhl | 600/18 |
| 4,448,190 | 5/1984 | Freeman | 600/18 |
| 4,453,537 | 6/1984 | Spitzer | 600/18 |
| 4,531,936 | 7/1985 | Gordon | 600/18 |

FOREIGN PATENT DOCUMENTS

| | | | |
|---|---|---|---|
| 2233293 | 1/1973 | Fed. Rep. of Germany | 600/18 |
| 1001928 | 3/1983 | U.S.S.R. | 604/96 |

OTHER PUBLICATIONS

Bregman et al., "Left Ventricular and Unidirectional Intraaortic Balloon Pumping," Journal of Thoracic and Cardiovascular Surgery, vol. 68, No. 5, 11-1974.
Dodge et al., "Usefulness and Limitations of Radiographic Methods for Determining Left Ventricular Volume," American Journal of Card., vol. 18, 7-1966.
Ross et al., "The Architecture of the Heart in Systole and Diastole," Circulation Research, vol. XXI, Oct. 1967.
Arvidsson, "Angiocardiographic Determination of Left Ventricular Volume," Acta Radiologica, vol. 56, Nov. 1961.
Donald et al., "Circulatory Support by a Left Ventricular Balloon Pump," Supplement I to Circulation, vols. XLIII and XLIV, May 1971.

Primary Examiner—Lee S. Cohen
Assistant Examiner—Kennedy J. Schaetzle
Attorney, Agent, or Firm—Pasquale A. Razzano

[57] ABSTRACT

Improved heart assist devices are disclosed. An improved heart assist device includes a catheter having a first lumen and a second lumen. An inflatable intraventricular balloon is located at the distal end of the catheter. The interior of the intraventricular balloon communicates with the first lumen of the catheter. An inflatable intraaortic balloon is located between the proximal and distal ends of the catheter. The interior of the intraaortic balloon communicates with the second lumen of the catheter. The heart assist device also includes a pumping mechanism that inflates and deflates both the intraventricular balloon and the intraaortic balloon. The improved heart assist device is inserted into the heart so that the intraventricular balloon is positioned in the left ventricle and so that the intraaortic balloon is positioned in the aorta. The intraventricular balloon is inflated during left ventricular systole, and the intraaortic balloon is deflated during left ventricular systole. The intraventricular balloon is deflated at the end of left ventricular systole or at the onset of left ventricular diastole, and the intraaortic balloon is inflated during left ventricular diastole. The inflation and deflation steps are repeated.

22 Claims, 10 Drawing Sheets

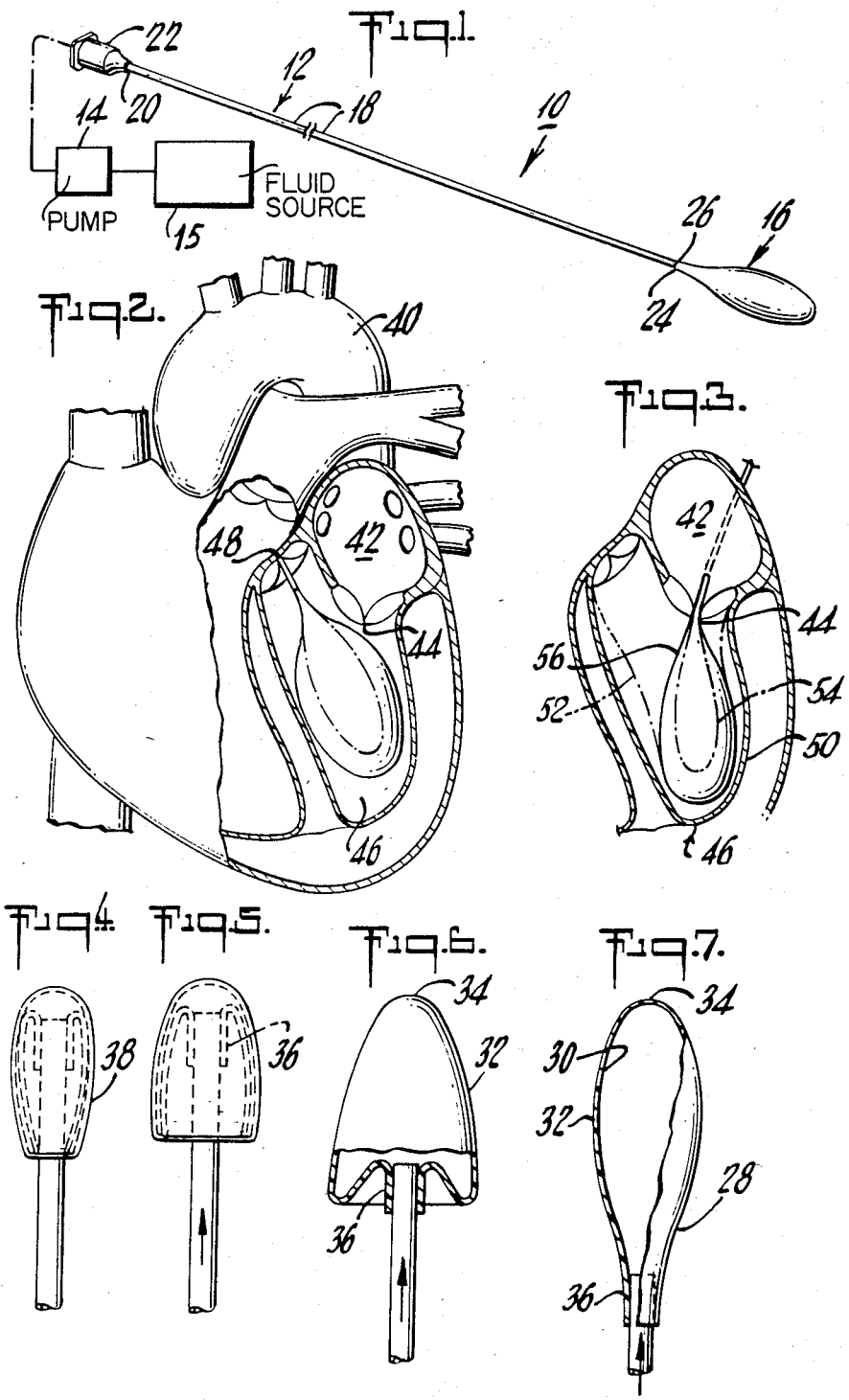

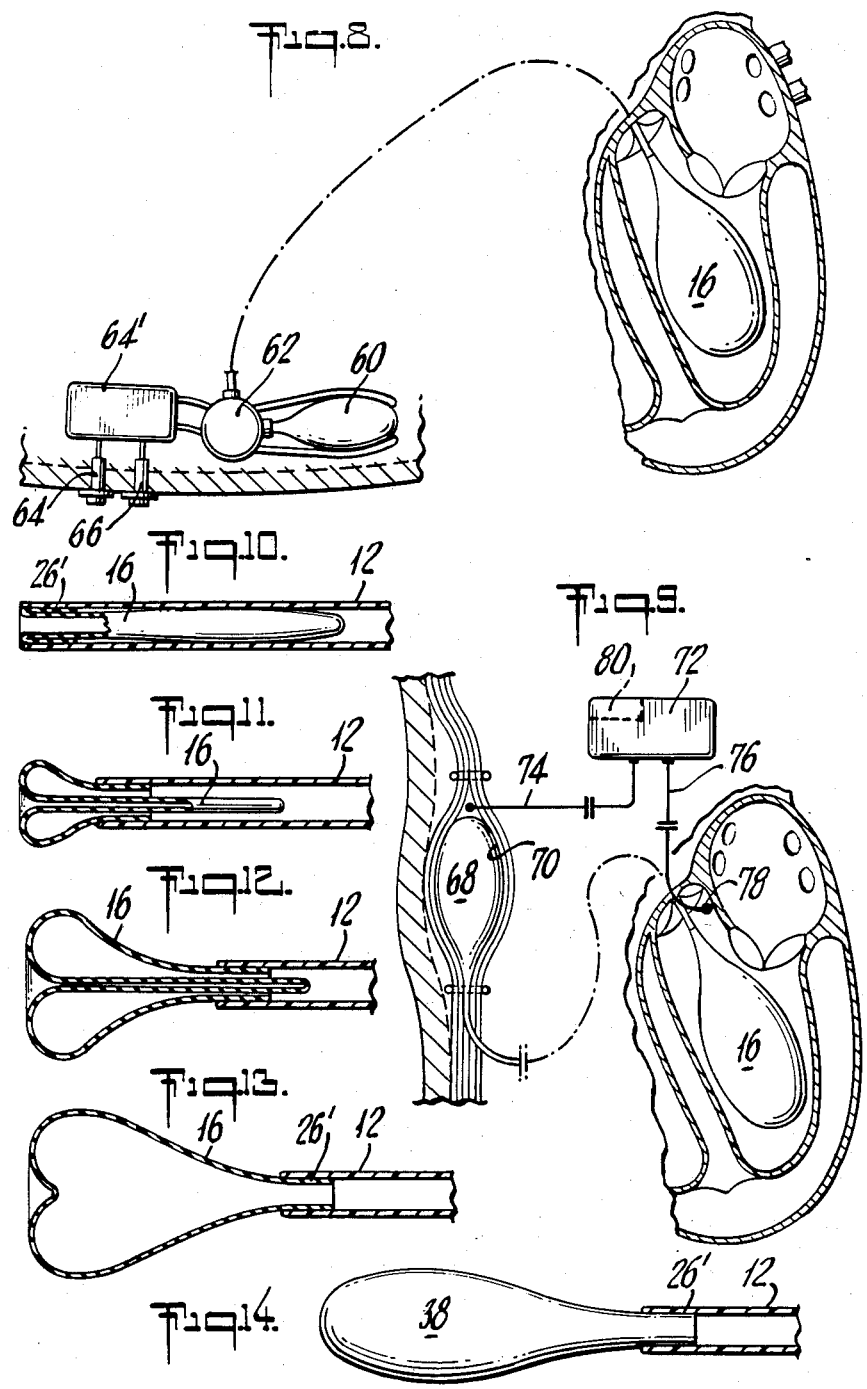

AORTIC FLOW

INTRAVENTRICULAR PRESSURE

HEART ASSIST DEVICE

CROSS REFERENCE TO RELATED APPLICATIONS

This application is a division of application Ser. No. 809,164, filed on Dec. 16, 1985, which is now U.S. Pat. No. 4,771.765. Application Ser. No. 809,164 was a continuation-in-part of application Ser. No. 582,118, filed on Feb. 21, 1985, which is now U.S. Pat. No. 4,685,446, issued on Aug. 11, 1987.

BACKGROUND OF THE INVENTION

The present invention relates to a new and improved heart assist device, and more specifically is directed to a device in which one expandable member is placed directly within the left ventricle of the heart and another expandable member is placed directly in the right ventricle of the heart or in the aorta to facilitate complete ejection of blood during systole.

In certain pathological conditions, the heart, and principally the left ventricle, cannot contract fully during systole, so there is incomplete emptying of the heart. The amount of blood remaining in the ventricle at the end of systole is the "dead volume" or "dead space" and represents unused pumping capacity.

Damage to the left ventricular muscle arises from a variety of causes, whether chemical, physical, bacterial and viral, and leads to a decrease of contractility and therefore to a decrease of ejection fraction. Consequently, congestive heart failure results, which may be correctable to varying degrees by pharmacological or mechanical intervention.

In intractable left ventricle failure, when it is not possible to increase the stroke volume, the "dead volume or space" at the end of the systole is increased.

The prior art devices appear generally to be in the nature of U.S. Pat. No. 3,266,487, which discloses devices that are placed within the aorta. None of the devices are placed directly within the left ventricle where they can operate more efficiently. U.S. Pat. No. 3,592,183 concerns a ventricular assist device having an aortic balloon with a somewhat similar shape to that of the present invention, but it does not perform the same functions, and it is not positioned within the left ventricle. U.S. Pat. No. 4,261,339 pertains to a device having an aortic balloon.

SUMMARY OF THE INVENTION

It is therefore an object of the present invention to provide an improved heart assist device which is designed to restore normal stroke volume.

A major object of the invention is to combine the benefits of a left ventricular balloon assist device with the benefits of an aortic balloon.

Another object of the present invention is to provide a device which restores normal stroke volume by reducing the dead volume or space at the end of systole in a damaged left ventricle.

Yet another object of the present invention is to provide a device of the character described which may be inserted directly into both the left ventricle and the right ventricle and operates with greater efficiency than prior art devices.

An additional object of the present invention is to provide a device of the character described which may be inserted directly into the left ventricle and placed in the aorta.

A further object of the present invention is to provide a device of the character described which may be implanted within the body of the user and is not tethered to any external operating elements.

Yet a further object of the present invention is to provide a device which only requires connection to an external electrical source.

Still another object of the present invention is to provide an improved device which will be easy to insert and yet be capable of operating at high efficiency.

Still a further object of the invention is to provide a device which will be simple and economical to manufacture and yet be durable to a high degree during the time of use required by the patient.

An improved heart assist device according to an embodiment of the invention includes a catheter having a first lumen and a second lumen. An inflatable intraventricular balloon is located at the distal end of the catheter. The interior of the intraventricular balloon communicates with the first lumen of the catheter. An inflatable intraaortic balloon is located between the proximal and distal ends of the catheter. The interior of the intraaortic balloon communicates with the second lumen of the catheter. The heart assist device also includes a pumping mechanism that inflates the intraventricular balloon while the intraaortic balloon is deflating and that inflates the intraaortic balloon while the intraventricular balloon is deflating.

The improved heart assist device is inserted into the heart so that the intraventricular balloon is positioned in the left ventricle and so that the intraaortic balloon is positioned in the aorta. The intraventricular balloon is inflated during left ventricular systole, and the intraaortic balloon is deflated during left ventricular systole. The intraventricular balloon is deflated when left ventricular systole ceases or when left ventricular diastole commences. Preferably, the intraventricular balloon is deflated as rapidly as possible. The intraaortic balloon is inflated during left ventricular diastole. The inflation and deflation steps are repeated. Accordingly, as the intraventricular balloon inflates, it pushes blood out of the left ventricle into the aorta. Then, as the intraaortic balloon inflates, it pushes blood out of the aorta antegrade and retrograde into the arteries.

Preferably, the pumping mechanism includes two pumps, one pump connected to the first lumen and another pump connected to the second lumen. The pumps advantageously inflate the balloons with either air, carbon dioxide, or helium. An electrocardiograph ("EKG") may sense the heart's electrical cycle and send signals to a control circuit for the pumping mechanism. The control circuit desirably controls the pumping mechanism to start inflation of the intraventricular balloon at approximately the beginning of left ventricular systole and to stop inflation of the intraventricular balloon at approximately the end of the left ventricular systole and further controls the pumping mechanism to start inflation of the intraaortic balloon at approximately the beginning of the left ventricular diastole and to stop inflation of the intraaortic balloon at approximately the end of left ventricular diastole. The pumping mechanism also actively deflates the intraventricular balloon and the intraaortic balloon. The intraventricular balloon may contain an amount of mercury sufficient to achieve neutral buoyancy or negative buoyancy at maximal inflation of the intraventricular balloon.

The heart assist device, including the pumping mechanism, may be implanted within a patient's body. If the pumping mechanism has two pumps, one of the pumps may be implanted within one envelope of skeletal muscle and the other pump may be implanted within another envelope of skeletal muscle. The cardiac electrical cycle is sensed, for example, with an EKG, and the envelopes of skeletal muscle are stimulated at appropriate times in response to the cardiac electrical cycle. Alternatively, the envelopes of skeletal muscle may be stimulated by signals from a pacemaker or a control relay.

An improved heart assist device according to another embodiment of the invention includes a catheter, a first tube connected to the distal end of the catheter, a first inflatable intraventricular balloon connected to the first tube, a second tube connected to the distal end of the catheter, and a second inflatable intraventricular balloon connected to the second tube. The heart assist device also includes a pumping mechanism that inflates the intraventricular balloons.

The first intraventricular balloon is inserted into the left ventricle of the heart, and the second intraventricular balloon is inserted into the right ventricle of the heart. The balloons may be inserted into the appropriate ventricle through the apex of the ventricle. The intraventricular balloons are inflated during ventricular systole and deflated either at the onset of ventricular diastole or at the end of ventricular systole. The inflation of the intraventricular balloons advantageously starts at approximately the beginning of ventricular systole and stops at approximately the end of ventricular systole. The balloons are actively deflated, preferably, as fast as possible. Rapid evacuation of the balloons results in a suction effect, which increases the flow of blood into the ventricle. Each of the intraventricular balloons may contain an amount of mercury sufficient to achieve neutral buoyancy or negative buoyancy at maximal inflation of the balloon.

The patient's heart may be monitored by an EKG, and the pumping mechanism may be controlled in response to signals from the EKG. The heart assist device, including the pumping mechanism, may be implanted within the patient's body. For instance, the pumping mechanism may be implanted within an envelope skeletal muscle. The envelope of skeletal muscle may be stimulated in response to the cardiac electrical cycle in order to actuate the pump, or the envelope of skeletal muscle may be stimulated by signals from a pacemaker or a control relay in order to actuate the pump.

An improved heart assist device according to yet another embodiment of the invention includes a catheter, first and second inflatable intraventricular balloons connected to the distal end of the catheter, and an intraaortic balloon located between the proximal end of the catheter and one of the intraventricular balloons. The heart assist device also includes a pumping mechanism. In use, the first and second intraventricular balloons are inserted into the left and right ventricles, while the intraaortic balloon is positioned in the aorta. The first and second intraventricular balloons are inflated and the intraaortic balloon is deflated during ventricular systole. The first and second intraventricular balloons are deflated and the intraaortic balloon is inflated during ventricular diastole.

BRIEF DESCRIPTION OF THE DRAWINGS

The above description, as well as further objects and advantages of the present invention, will be more fully appreciated with reference to the following detailed description of preferred, but nonetheless illustrative, embodiments of the invention, when taken in conjunction with the following drawings, wherein:

FIG. 1 is a front perspective view of an improved ventricular assist device;

FIG. 2 is a view of the heart showing the device of FIG. 1 in a temporary installation passing through the aortic valve in its inflated state in solid line and in its deflated state in dotted line;

FIG. 3 is a view similar to FIG. 2, but primarily of the left ventricle showing the device in a permanent installation passing through the mitral valve in its inflated state in solid line and in its deflated state in dotted line;

FIG. 4 is a view showing the balloon in the collapsed configuration folded back along the catheter for insertion;

FIG. 5 is a view similar to FIG. 4 with the balloon partially inflated;

FIG. 6 is a view similar to FIG. 5 with the balloon further inflated;

FIG. 7 shows the balloon at the distal end of the catheter in its operating, fully inflated state;

FIG. 8 is a schematic view of a structure permanently implanted in subcutaneous fat but with external electrical terminals;

FIG. 9 is a schematic view of another structure completely permanently implanted within a patient's body;

FIGS. 10, 11, 12, 13, and 14 are views of the balloon packaged in another manner to facilitate insertion via an artery or through the left atrium, from the deflated state, and with inflation, gradually extending itself beyond the end of the catheter;

DETAILED DESCRIPTION OF THE PREFERRED EMBODIMENTS

Figure 15:
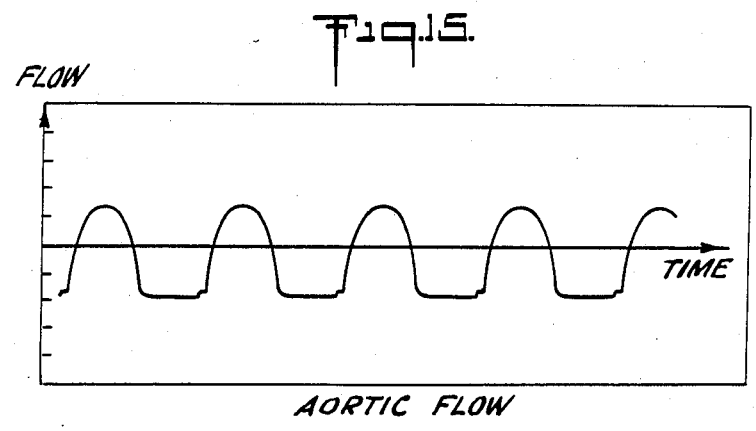
FIG. 15 is a graph illustrating aortic flow.

Referring to the drawings, and in particular to FIG. 1, there is shown an improved ventricular assist device 10 broadly comprising a catheter 12, a pump 14 (shown in schematic), a fluid source 15, and an inflatable balloon 16.

The catheter is generally made of plastic or a woven synthetic material and is a standard flexible hollow catheter defined by an outer surface 18, a proximal end 20 to which is secured an attachment member 22 for making a connection to the pump 14, and a distal end 24 having either a securement device or bonding means 26. The bonding means 26 is used to secure the balloon 16 to the distal end 24.

Turning more particularly to FIG. 7, the balloon includes a wall 28 defined by an inner surface 30 and an outer surface 32. For percutaneous insertion through a dilator, the balloon is folded so that it overlaps itself forming a crown 38 as in FIG. 4. Alternatively, it may be packaged inverted on itself inside the lumen of the catheter as in FIG. 10. Both configurations are to provide a minimal cross-sectional area to facilitate insertion. The balloon is securely attached to the distal end 24 of the catheter 18 by bonding 26, for example, as at 36, to provide an air-tight seal between the neck of the balloon and the catheter. FIGS. 5 and 6 illustrate the balloon during progressive stages of inflation.

The pump unit 14 is similar to existing pumps used to drive intraaortic balloon assist devices and is activated at specific points in the cardiac cycle.

FIG. 2 shows a representation of the heart with the aorta 40 leading away from the opposite side of the left atrium 42. The left atrium ends at the mitral valve 44, which then leads into the left ventricle 46. The aortic valve 48 provides the exit from the left ventricle.

Turning to FIG. 3, there is shown a representation of the operation of the ventricular assist device. The outer solid line shows the maximum diastolic margin 50 of the inner ventricular wall and the maximum end systolic margin is shown in dotted line 52. The inflated balloon is shown in solid line 56 and the deflated balloon is shown in dotted line 54. The installation through the mitral valve 44 as shown in this figure is a permanent installation as opposed to a temporary installation through the aortic valve, which is illustrated in FIG. 2. A permanent installation may also be accomplished by inserting the balloon through the apex of the left ventricle.

In order to use the ventricular assist device, the end systolic volume and shape of the left ventricle is determined by imaging techniques, such as two-dimensional echocardiography or isotope tomography. For example, techniques for determining left ventricular volume are disclosed in an article entitled "Usefulness and Limitations of Radiographic Methods for Determining Left Ventricular Volume," by H. T. Dodge, H. Sandler, W. A. Baxley, and R. R. Hawley, which was published in *The American Journal of Cardiology*, Volume 18, July 1966, at pages 10–24. An article entitled "The Architecture of the Heart in Systole and Diastole," by J. Ross, Jr., E. H. Sonnenblick, J. W. Covell, G. A. Kaiser, and D. Spiro, which was published in *Circulation Research*, Volume XXI, No. 4, October 1967, at pages 409–421, and an article entitled "Angiocardiographic Determination of Left Ventricular Volume," by H. Arvidsson, which was published in *ACTA Radiologica*, Volume 56, November 1961, at pages 321–339, also describe methods for measuring left ventricular volume. A preformed balloon that is just smaller than this chamber size and shape is selected. The balloon device is deflated and allowed to completely collapse as shown in FIG. 4 with the overlapping portions folded over the distal end 24 of the catheter 18. A guide wire is inserted into the femoral artery via a needle, and the needle is withdrawn. A series of increasingly larger cannulas are inserted over the guide wire until a final cannula large enough to admit the folded balloon-catheter tip combination is left in place, and the balloon catheter inserted and threaded retrograde, through the aortic valve, into the left ventricle. To achieve neutral buoyancy at maximal inflation, an appropriate amount of mercury is introduced via the catheter into the balloon. The cannula is then removed. The proximal end 20 of the catheter is connected to the pump 14, which is then activated by an EKG monitoring the patient, so that inflation of the balloon begins with the onset of the left ventricular systole and is completed at the end of systole. Inflation of the balloon occurs during the ventricular systolic interval, and deflation occurs at the end of systole or at the start of diastole.

The volume of gas, e.g., carbon dioxide or helium, to be pumped in and exhausted will be determined by assessment of the "dead volume" or "dead space" at the end of systole. Various existing techniques, such as ultrasound imaging or gated isotope scanning, may be used to arrive at this volume. The pump will be set so the fully inflated balloon will completely fill the dead volume.

This will eliminate the intraventricular dead volume created by incomplete systolic contraction of the ventricle. Since mitral valve closure and aortic valve opening mandate unidirectional flow, this dead volume of blood is ejected into the ascending aorta by the kinetic energy of the expanding balloon, and adds to the total ejection volume. It further facilitates diastolic filling of the left ventricle by increasing the negative pressure in the ventricle as the balloon is actively deflated.

The entire sequence described above is repeated with the end of diastole and the beginning of systole.

When used as a permanent "artificial heart," the balloon is implanted through open heart surgery with the route of entry through the left atrium, so that the catheter traverses the mitral valve. As stated previously, it can also be inserted through a small incision in the apex. The catheter is led out through the chest wall and connected to the pump which, of course, is extracorporeal.

FIG. 10 illustrates a modified construction for positioning the deflated balloon 16 within the catheter 12 during insertion. The largest external diameter during insertion is that of the catheter, while in the construction shown in FIG. 4, the diameter extends to the outer surface 38 of the deflated balloon. The balloon is secured to the inner wall as at 26' FIGS. 11-13 show the balloon during progressive stages of inflation, and FIG. 14 illustrates the fully inflated balloon.

FIG. 8 illustrates a modified construction in which the entire device, except for the power leads, is implanted subcutaneously. The balloon 16 is connected to a gas reservoir 60 which may be implanted in the abdominal fat and which is surrounded by a solenoid activated electromagnetic bellows-type pump 62. The unit is activated by a control unit 64' which senses the cardiac electrical cycle. Wires 64, 66 extend through the skin and can be connected to an external power pack (not shown) which may be carried by the patient in a shoulder holster (not shown).

FIG. 9 illustrates another modified construction which is self-contained under the skin of a patient. The balloon 16 is attached to a reservoir 68 positioned within an envelope 70 of skeletal muscle, constructed from either the pectoral or the anterior rectus muscles of the abdomen. This "envelope" or "muscle pump" is paced by a control relay 72 electrically connected by leads 74, 76 to the envelope 70 and the sinus node 78 of the heart, or the muscle pump may be activated by a standard pacemaker. The relay is powered by a long-life lithium battery 80. The relay is activated by the sinus node and initiates contraction of the muscle pump at the onset of mechanical systole, and allows relaxation at the onset of diastole.

The balloon 16 used in the construction of FIGS. 8 and 9 is made of thicker material than the reservoirs 60, 68 so that it will normally deflate, thereby inflating the reservoirs.

Supplementary Data

The ventricular assist device as described above has been tested in vitro and in vivo.

In Vitro

In the vitro system, an artificial circulatory system was constructed consisting of the following components:

(1) a clear plexiglass chamber (left ventricle);
(2) an inlet port with a one-way valve (mitral valve);
(3) an outlet port (aorta) with a one way (aortic valve);
(4) plastic tubing leading from the outlet port to an air damper; and
(5) plastic tubing leading from the air damper to the inlet port.

Through an air-tight seal the balloon was inserted into the chamber-ventricle. A pressure transducer was placed in the chamber to measure "intraventricular pressure." An electromagnetic flow meter was placed around the exit port (aorta). The balloon was connected to a 50 ml. syringe. The circulatory system was filled with saline. The balloon was alternately inflated and deflated with air to a volume of 40 ml. at a rate of 24 times per minute.

Figure 16:
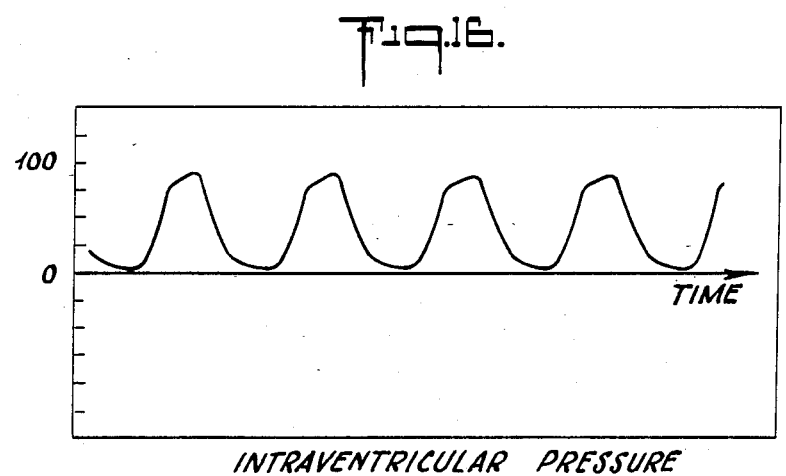
FIG. 16 is a graph illustrating intraventricular pressure.

Results are shown on the graphs depicted in FIGS. 15 and 16. An intraventricular pressure of 100 mm. Hg. and an aortic flow of 1500 ml. per minute were generated.

In Vivo

A 20 kg. mongrel dog was anesthetized and the heart exposed with a thoracotomy. Respiration was maintained through an endotracheal tube with a respirator. A 0.5-cm. incision was made in the apex of the left ventricle, and the ventricular assist device ("VAD") inserted into the ventricle. The heart was arrested in diastole with an IV infusion of 10% KCl. The balloon was activated by hand pumping with a 50 ml. syringe to a volume of 40 ml. at 25 cycles per minute. This was continued for 15 minutes during which time respiration was maintained with the respirator, and the heart action was totally stopped. At the end of 15 minutes, balloon assist was stopped. It was possible then to restore normal cardiac contraction by manual cardiac massage.

The implication of this experiment is that had coronary perfusion not been maintained during the 15 minutes of balloon assist, it would have been impossible to restart the heart. Obviously, then, the balloon VAD was effective in maintaining coronary flow sufficient to keep the myocardium alive and responsive to cardiac massage resuscitation. The strong implication is that normal cardiac output was maintained although the ventricle was completely stopped.

Aortic pressure during this experiment was 200/0. Aortic flow was measured with a Doppler sensor, so no absolute values are available.

Figure 17:
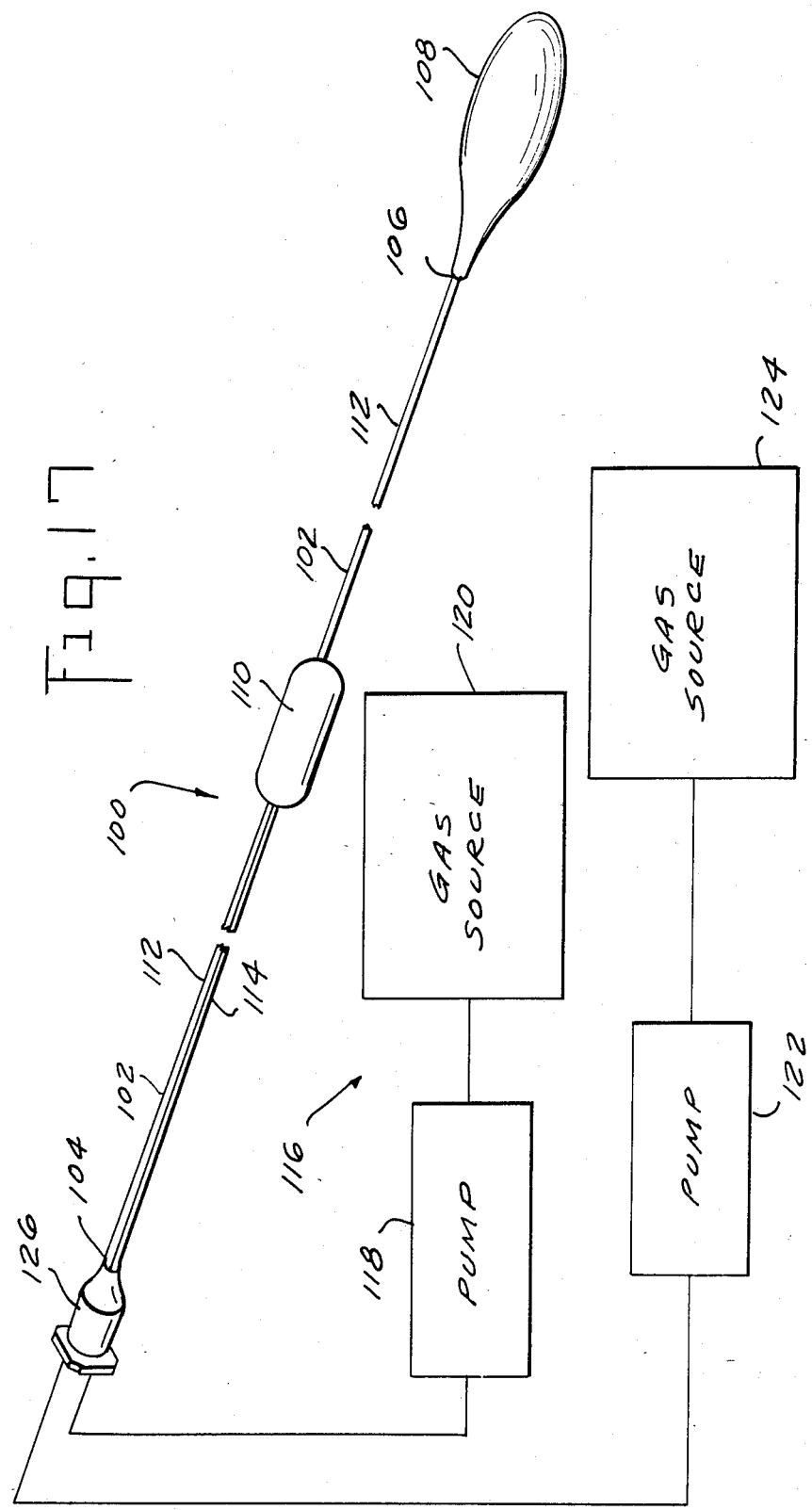
FIG. 17 is a perspective view of an improved heart assist device.

An improved heart assist device according to the invention is illustrated in FIG. 17. The heart assist device, which is generally designated by the reference numeral 100, includes a catheter 102, with a proximal end 104 and a distal end 106, an inflatable intraventricular balloon 108, and an inflatable intraaortic balloon 110. The catheter 102 is similar in construction to the catheter 12 of the ventricular assist device 10, which is described above. Additionally, the intraventricular balloon 108 is similar in construction to the balloon 16 of the ventricular assist device 10. The intraventricular balloon 108 is located at the distal end 106 of the catheter 102. The catheter 102 has two lumens 112 and 114. The interior of the intraventricular balloon 108 communicates with the lumen 112, while the interior of the intraaortic balloon 110 communicates with the lumen 114. The intraventricular balloon 108 is sized in the same manner as the balloon 16 of the ventricular assist device 10. The intraaortic balloon 110 is sized in a conventional manner.

The heart assist device 100 also includes a pumping mechanism, which is generally denoted by the reference numeral 116. The pumping mechanism 116 inflates the intraventricular balloon 108 and the intraaortic balloon 110. The pumping mechanism 116 has a first pump 118, which pumps gas from a first gas source 120, and a second pump 122, which pumps gas from a second gas source 124. The pump 118 is connected through an attachment member 126 to the lumen 112 of the catheter 102. Accordingly, the pump 118 is used to inflate and deflate the intraventricular balloon 108. The pump 122 is connected through the attachment member 126 to the lumen 114 of the catheter 102. Consequently, the pump 122 is used to inflate and deflate the intraaortic balloon 110. Each of the pumps 118 and 122 both inflates and deflates, i.e., evacuates, the associated balloon.

Each of the gas sources 120 and 124 advantageously contains either air, carbon dioxide, or helium. Air is the least expensive of these gases. However, if a leak occurs, carbon dioxide is the safest of these gases. Helium has the lowest specific gravity and, therefore, is the easiest to pump. The selection of the gas actually utilized depends upon a number of design constraints.

While two gas sources are illustrated in FIG. 17, a single gas source may be employed. If a single gas source is used, each of the pumps 118 and 122 would be connected to it.

Figure 18:
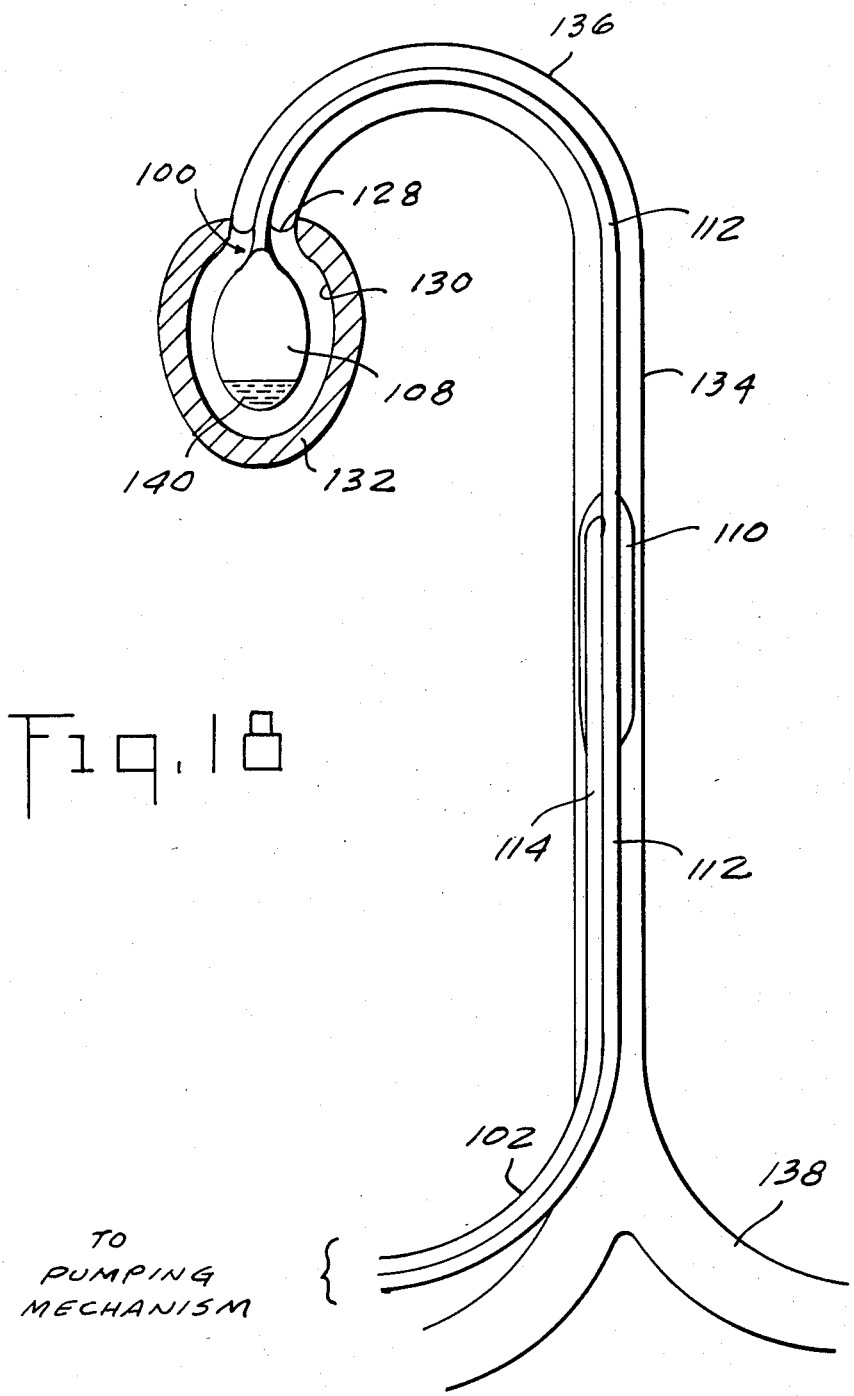
FIG. 18 is a diagrammatic illustration of an improved heart assist device.

FIG. 18 schematically depicts the heart assist device 100 after it has been installed within the body of a patient. The intraventricular balloon 108 is inserted through the aortic valve 128 into the left ventricle 130 of the heart 132. The intraaortic balloon is positioned in the aorta 134 beyond the aortic arch 136. The catheter 102 may exit the aorta 134 at about the point where the femoral artery 138 branches off the aorta 134. The intraventricular balloon 108 contains mercury 140, which is used to weight the balloon. The purpose of weighting the balloon is discussed below.

Figure 19:
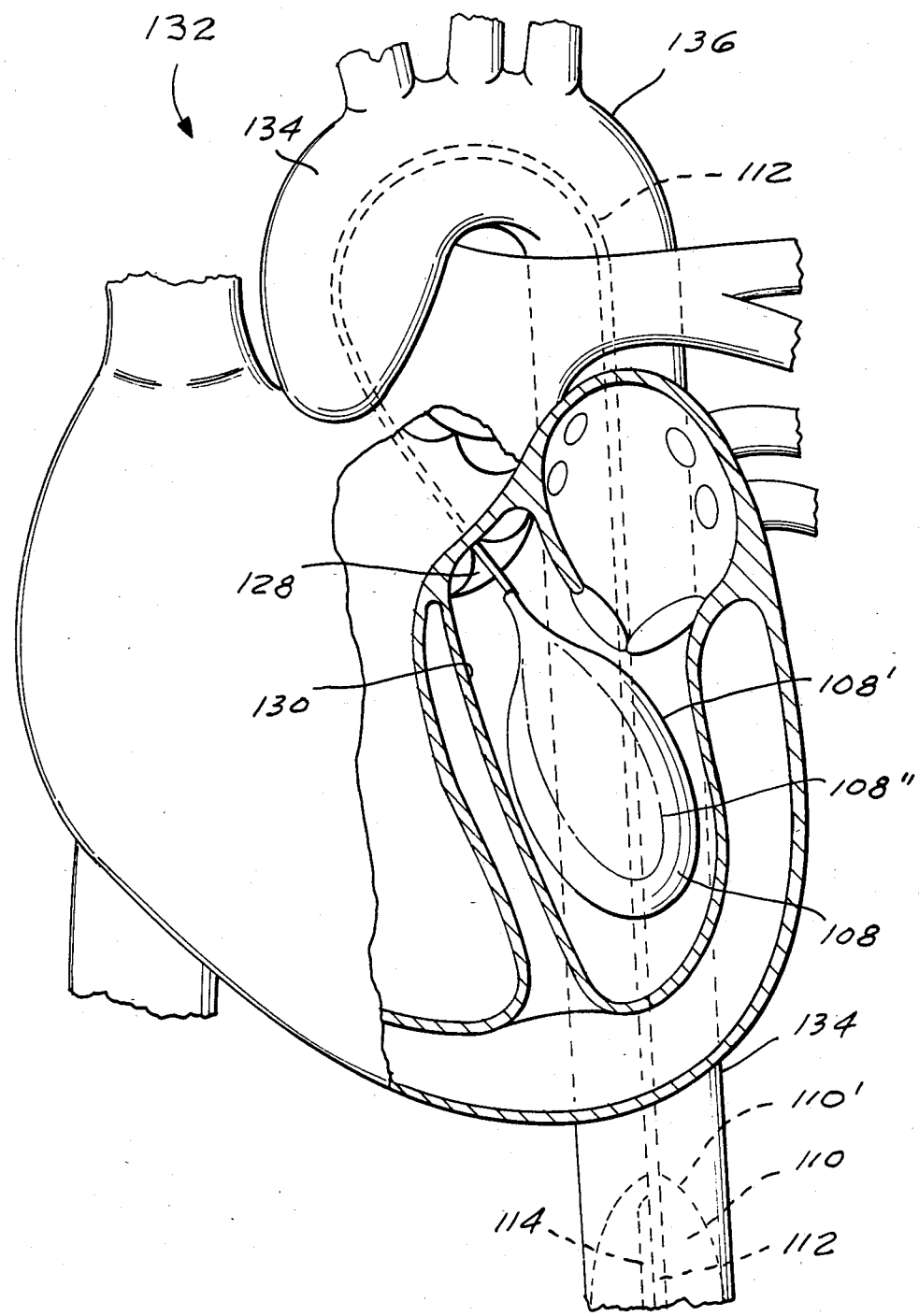
FIG. 19 is a view of a heart, with parts broken away for clarity, showing an improved heart assist device after installation.

FIG. 19 shows the heart assist device 110 in use. As noted above, the intraventricular balloon 108 may be inserted through the aortic valve 128 into the left ventricle 130 of the heart 132. Again, the intraaortic balloon 110 is located in the aorta 134 beyond the aortic arch 136. The solid line 108' for the intraventricular balloon 108 shows the balloon 108 when it is fully inflated, while the line 108" with long and short dashes shows the balloon 108 when it is deflated. The dashed line 110' for the intraaortic balloon 110 depicts the balloon 110 when it is fully inflated.

A control circuit for the pumps 118 and 122 controls them to alternately inflate the balloons 108 and 110. That is, the balloons 108 and 110 are inflated during different periods of the cardiac electrical cycle. The balloons 108 and 110 are, correspondingly, deflated during different periods of the cardiac electrical cycle. The pump 118 inflates the intraventricular balloon 108 while the pump 122 evacuates the intraaortic balloon 110.

The intraventricular balloon 108 is inflated during left ventricular systole, and the intraaortic balloon 110 is inflated during left ventricular diastole. Thus, during left ventricular systole, the intraventricular balloon 108 forces blood out of the left ventricle 130 into the aorta 134. The intraaortic balloon 110 is deflating or deflated during this time. Consequently, blood flows from the left ventricle 130 into the aorta 134, past the intraaortic balloon 110. Subsequently, during left ventricular diastole, the intraaortic balloon 110 inflates, thereby forcing blood out of the aorta 134 and into the arteries.

A heart assist device having an intraventricular balloon and an intraaortic balloon, such as the device 100, may be used in certain circumstances where a ventricular assist device having only an intraventricular balloon, such as the device 10, may be ineffective. For example, in some situations the flow rate from the heart may be inadequately low even if a ventricular assist device with an inflatable balloon is inserted directly into the left ventricle and operated as described above. However, by including an intraaortic balloon the flow rate may be increased so that it is sufficient for the patient.

The intraventricular balloon 108 desirably contains mercury, as mentioned previously. The intraventricular balloon 108 may contain an amount of mercury sufficient to achieve neutral buoyancy or negative buoyancy at maximal inflation of the balloon. In other words, mercury is employed to weight the intraventricular balloon 108 and cause it to remain low within the left ventricle, even when the intraventricular balloon 108 is fully inflated. An unweighted intraventricular balloon may undesirably rise within the left ventricle while it is being inflated and block the aortic valve, thereby blocking the flow of blood. FIG. 18 depicts mercury 140 within the intraventricular balloon 108. However, mercury is unnecessary if the intraventricular balloon is inserted into the ventricle through the apex of the ventricle.

The amount of mercury necessary to achieve neutral or negative buoyancy at maximal inflation of the intraventricular balloon may be calculated by measuring the blood hemoglobin and determining the specific gravity of the blood. Then, the fully inflated size of the balloon is ascertained from the specifications for the heart assist device, such as the size of the intraventricular balloon, the resiliency of the intraventricular balloon, and the power of the pump. From the specific gravity of the blood and the fully inflated size of the balloon, the proper amount of mercury may be determined.

Figure 23:
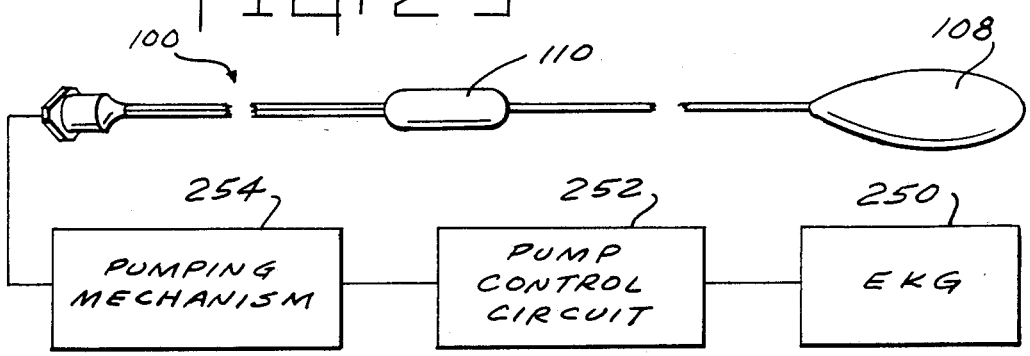
FIG. 23 is a schematic diagram of a heart assist device together with sensing and control circuits.
Figure 24:
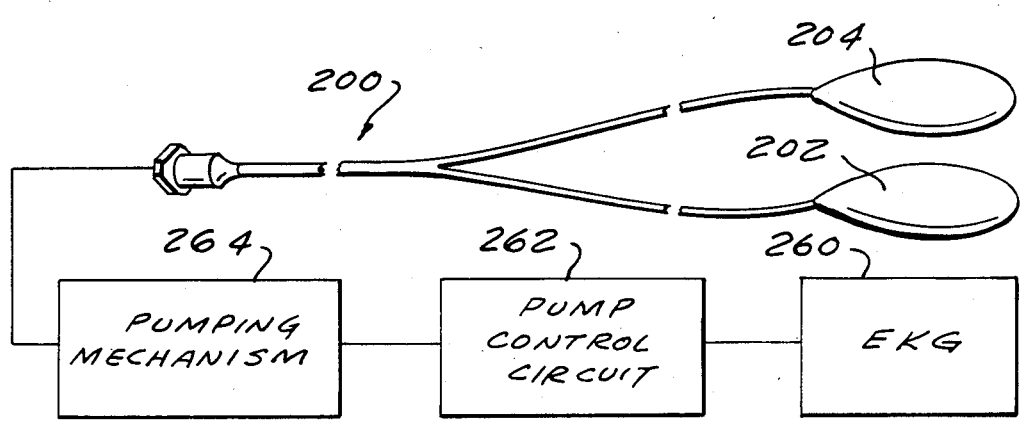
FIG. 24 is another schematic diagram of a heart assist device together with sensing and control circuits.

An EKG may be utilized to sense the cardiac electrical cycle, as noted above. The EKG then sends output signals to a pump control circuit, which controls the actuation of the pumps 118 and 122 and, therefore, the inflation of the balloons 108 and 110. FIGS. 23 and 24 each illustrate an EKG that monitors the cardiac electrical cycle and sends output signals to a pump control circuit. Preferably, the pus 118 and 122 are controlled so that inflation of the intraventricular balloon 108 and deflation of the intraaortic balloon 110 start at approximately the beginning of the left ventricular systole and stop at approximately the end of left ventricular systole and so that inflation of the intraaortic balloon 110 starts at approximately the beginning of the left ventricular diastole and stops at approximately the end of left ventricular diastole. The intraventricular balloon 108 is advantageously deflated at the end of left ventricular systole or at the beginning of left vetricular diastole. The intraventricular balloon 108 is advantageously deflated as quickly as possible, which causes a suction effect in the left ventricle 130, thereby enhancing the flow of blood into the left ventricle 130.

Figure 22:
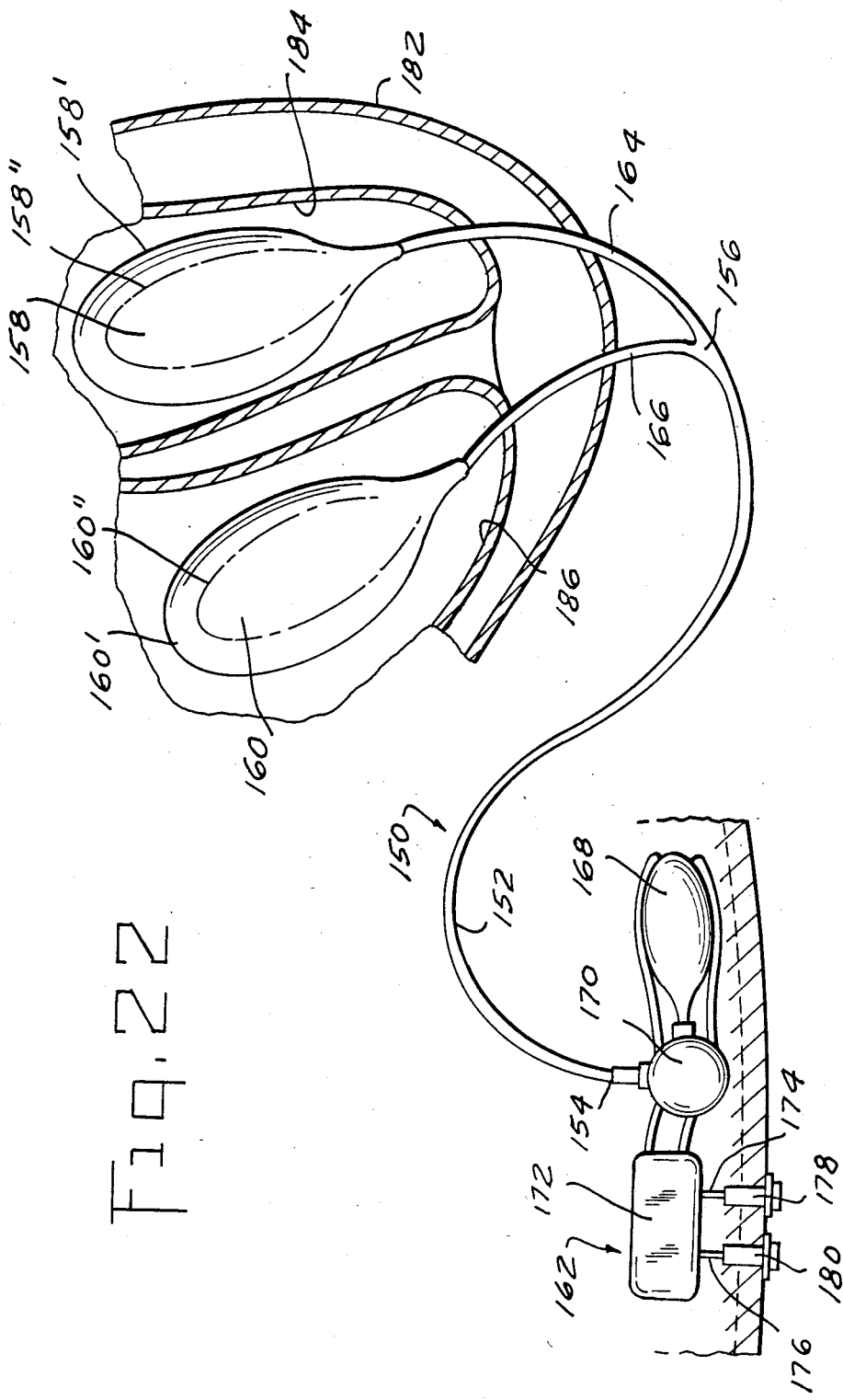
FIG. 22 is a schematic illustration of an improved heart assist device that is implanted within a patient.

Another improved heart assist device according to the invention is illustrated in FIG. 22. The heart assist device, which is generally designated by the reference numeral 150, includes a catheter 152, with a proximal end 154 and a distal end 156, a first inflatable intraventricular balloon 158, a second inflatable intraventricular balloon 160, and a pumping mechanism 162. The catheter 152 may be constructed like the catheter 12, described above, and the balloons 158 and 160 may be constructed like the balloon 16, described above. The intraventricular balloons 158 and 160 are connected through tubes 164 and 166, respectively, to the distal end 156 of the catheter 152. Consequently, the interiors of the balloons 158 and 160 communicate through the tubes 164 and 166, respectively, with the lumen of the catheter 152.

The pumping mechanism 162 is similar to the pumping mechanism shown in FIG. 8, which is discussed above. The pumping mechanism 162 has a gas reservoir 168, a pump 170, and a control unit 172. Leads 174 and 176 extend from the control unit 172 to terminals 178 and 180, respectively, which are located on the surface of the skin. Accordingly, the pumping mechanism 162 may be energized by an external power supply (not shown), which may be connected to the terminals 178 and 180. The pump 170 is actuated at appropriate times by the control unit 172 to inflate and deflate the intraventricular balloons 158 and 160.

FIG. 22 depicts a heart 182 with a left ventricle 184 and a right ventricle 186. The intraventricular balloon 158 is inserted into the left ventricle 184 through the apex of the left ventricle. The intraventricular balloon 160 is inserted into the right ventricle 186 through the apex of the right ventricle. Although FIG. 22 shows one way in which the balloons 158 and 160 may be inserted into the ventricles, the balloons 158 and 160 may be inserted into the ventricles at other locations. For instance, the balloon 160 may be inserted into the right ventricle 186 through the tricuspid valve, with the tube 166 traveling through the inferior vena cava or the superior vena cava. Moreover, the balloon 158 may be inserted into the left ventricle 184 through the aortic valve.

The pump 170 inflates the balloons 158 and 160 simultaneously. Left ventricular systole and right ventricular systole begin and end at about the same times. Similarly, left ventricular diastole and right ventricular diastole begin and end at about the same times. Therefore, the inflation and deflation of the balloons 158 and 160 may be timed to coincide with either right ventricular systole and diastole or left ventricular systole and diastole. The pump 170 may be controlled to start inflating the balloons 158 and 160 at approximately the beginning of ventricular systole and to stop inflating the balloons 158 and 160 at approximately the end of ventricular systole. The pump 170 may be controlled to deflate the balloons 158 and 160 as rapidly as possible at the onset of ventricular diastole. The solid lines 158' and 160' show the balloons 158 and 160, respectively, when inflated, while the dashed lines 158" and 160" depict the balloons 158 and 160, respectively, when deflated. The balloons 158 and 160 become fully inflated at approximately the same time.

The balloon 158 may be sized in the same manner as the balloon 16 of the ventricular assist device 10. The balloon 158 should completely fill the dead volume in the left ventricle when it is fully inflated. The balloon 160 may be sized in a similar manner. The dead volume in the right ventricle may be determined by the same techniques utilized to determine the dead volume in the left ventricle. The balloon 160 should completely fill the dead volume in the right ventricle when it is fully inflated.

Since the pressure in the right ventricle 186 is lower than the pressure in the left ventricle 184, the balloon 160 is advantageously less elastic than the balloon 158. In other words, the balloon 160 has a greater resistance to changing its volume than the balloon 158. That is, the balloon 160 has a greater resistance to the pump 170 than the balloon 158. This difference in the resiliency of the balloons 158 and 160 compensates for the difference in the pressures of the left and right ventricles. Alternatively, an orifice may be included in the tube 166 to compensate for the difference in the pressures of the left and right ventricles.

Although FIG. 22 illustrates the balloons 158 and 160 being inflated by a single pump 170, other arrangements are possible. For example, the catheter 152 may be replaced by a two-lumen catheter, and one pump may be connected to each of the lumens. The two pumps may be independently controlled s that the two balloons are independently inflated and deflated.

Figure 20:
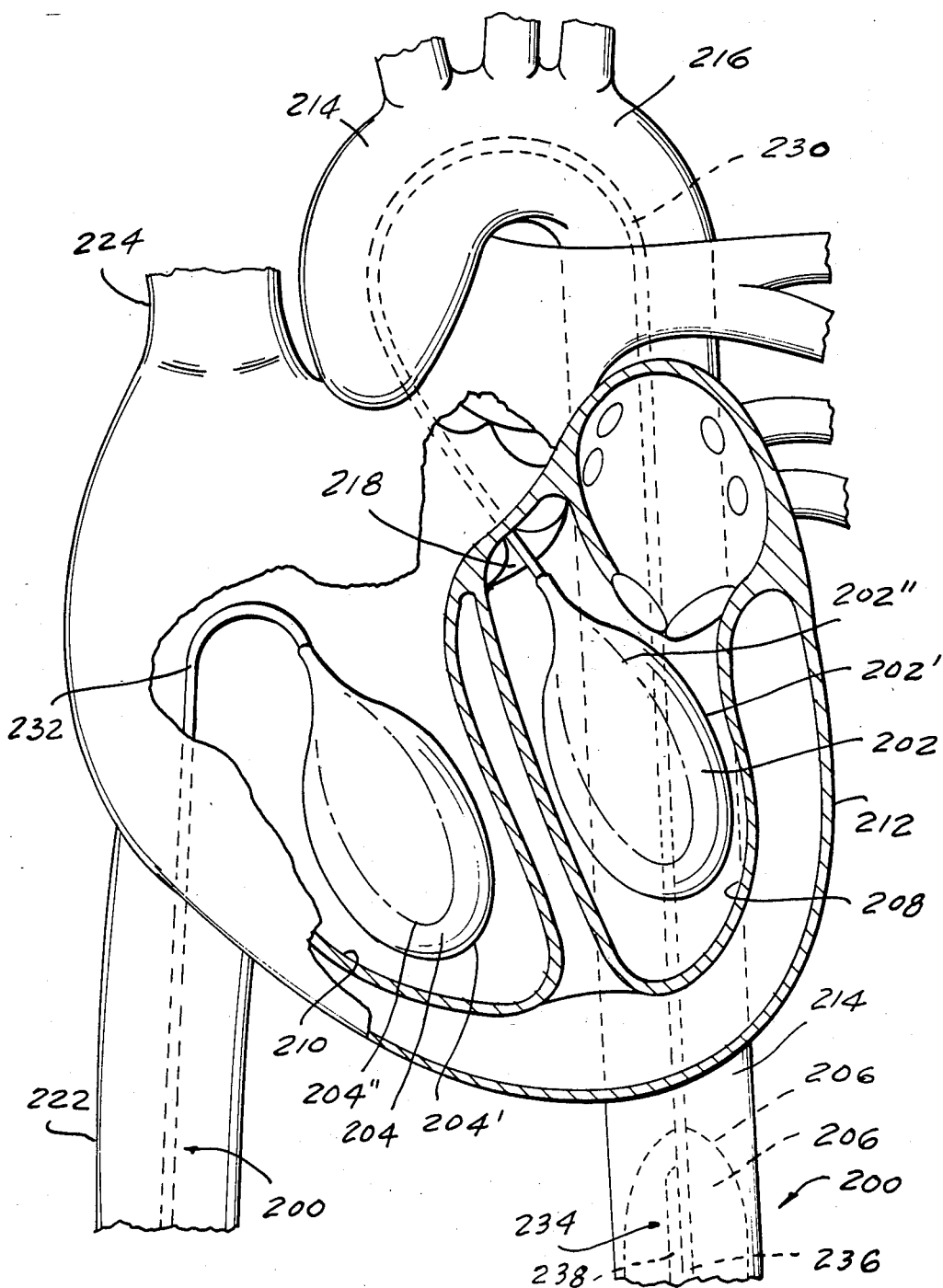
FIG. 20 is another view of a heart, with parts broken away for clarity, showing another improved heart assist device after installation.

A modification of the heart assist device 150 depicted in FIG. 22 is illustrated in FIG. 20. FIG. 20 shows a heart assist device, which is generally designated by the reference numeral 200, having two intraventricular balloons 202 and 204 and an intraaortic balloon 206. The intraventricular balloons 202 and 204 are inserted into the left ventricle 208 and the right ventricle 210, respectively, of the heart 212. The intraaortic balloon 206 is positioned in the aorta 214 beyond the aortic arch 216. The intraventricular balloon 202 enters the left ventricle 208 through the aortic valve 218, while the intraventricular balloon 204 enters the right ventricle 210 through the tricuspid valve (not shown).

The intraventricular balloons 202 and 204 are connected through tubes 230 and 232, respectively, to a catheter 234, but for ease of illustration, the connection between the tube 232 and the catheter 234 is not shown. The catheter 234 has two lumens 236 and 238, like the catheter 102 discussed previously. The construction of the catheter 234 may be similar to the construction of the catheter 102. The interiors of the intraventricular balloons 202 and 204 communicate through the tubes 230 and 232, respectively, with the lumen 236 of the catheter 234. The interior of the intraaortic balloon 206 communicates with the lumen 238 of the catheter 234. The proximal end of the catheter is connected to a pumping mechanism (not shown), such as the pumping mechanism 116, which is illustrated in FIG. 17 and described above.

The pumping mechanism is controlled to inflate the intraventricular balloons 202 and 204 and deflate the intraaortic balloon 206 during ventricular systole and to inflate the intraaortic balloon 206 during ventricular diastole. The pumping mechanism is controlled to deflate the intraventricular balloons 202 and 204 at about the start of ventricular diastole or at about the end of ventricular systole. The solid lines 202' and 204' illustrate the inflated balloons 202 and 204, respectively, while the dashed lines 202" and 204" depict the deflated balloons 202 and 204, respectively. The dashed line 206' shows the inflated balloon 206. The intraventricular balloons 202 and 204 force blood out of the associated ventricle when they are inflating and allow the associated ventricle to fill when they are deflating. The intraaortic balloons 206 urges blood further into the aorta and into the arteries when it is inflating.

FIG. 20 depicts the tube 232 traveling through the inferior vena cava 222. However, the tube 232 may be routed through the superior vena cava 224. Additionally, FIG. 22 illustrates the balloons 202 and 204 entering the left ventricle 208 and the right ventricle 210, respectively, through the aortic valve and the tricuspid valve, respectively. However, the intraventricular balloons may be inserted into the associated ventricles at other locations. For instance, the intraventricular balloons may be inserted into the associated ventricle through the apex of the associated ventricle. Such an installation is shown in FIG. 22.

The intraventricular balloons 202 and 204 are constructed and sized like the intraventricular balloons 158 and 160 of the device 150. The intraaortic balloon 206 is constructed and sized like the intraaortic balloon 110 of the device 100. The intraventricular balloons may contain an amount of mercury sufficient to achieve neutral buoyancy or negative buoyancy at maximal inflation of the balloon.

Figure 21:
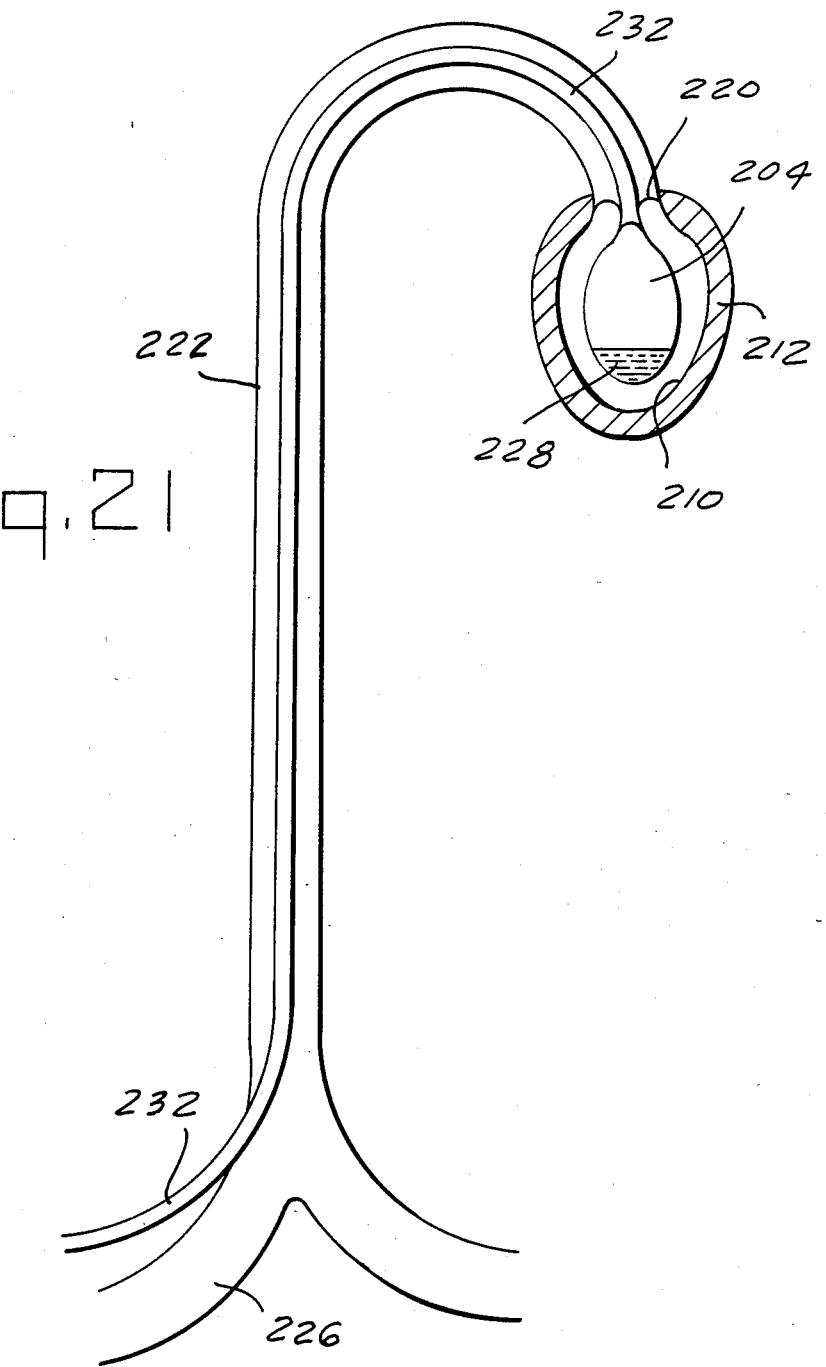
FIG. 21 is a diagrammatic illustration of another improved heart assist device.

FIG. 21 schematically illustrates part of the heart assist device 200. The tube 232 is routed through the inferior vena cava 222 and enters the right ventricle 210 through the tricuspid valve 220. In this fashion, the intraventricular balloon 204 is inserted into the right ventricle 210. The tube 232 may exit the inferior vena cava 222 at about the point where the hepatic vein 226 joins the inferior vena cava 222. As shown in FIG. 21, the intraventricular balloon 204 contains mercury 228, which weights the balloon.

Figure 25:
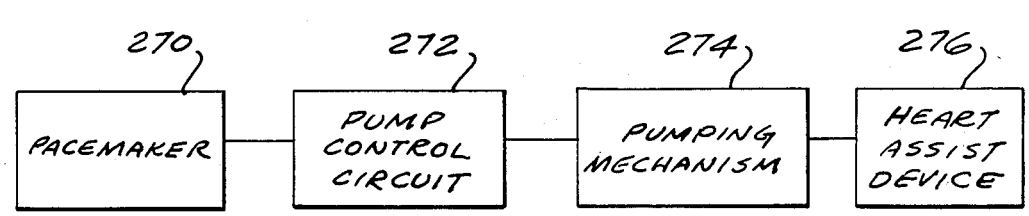
FIG. 25 is a block diagram of a heart assist device and associated control circuits.

FIGS. 23, 24, and 25 are schematic diagrams of heart assist devices, including pumping mechanisms, and control circuits. In FIG. 23, an EKG 250 monitors the cardiac electrical cycle through a number of leads (not shown) attached to a patient. The EKG 250 sends signals to a pump control circuit 252. The pump control circuit 252 is connected to a pumping mechanism 254. The pump control circuit 252 provides control signals for actuating the pump or pumps in the pumping mechanism 254 so that the balloons 108 and 110 of the heart assist device 100 are inflated and deflated at suitable times during the cardiac electrical cycle, as described above. In FIG. 24, an EKG 260 monitors the cardiac electrical cycle through a number of leads (not shown) attached to a patient. The EKG 260 sends signals to a pump control circuit 262. The pump control circuit 262 is connected to a pumping mechanism 264. The pump control circuit 262 provides control signals for actuating the pump or pumps in the pumping mechanism 264 so that the balloons 202 and 204 of the heart assist device 200 are inflated and deflated at suitable times during the cardiac electrical cycle, as described above.

FIG. 25 illustrates another pump control circuit configuration. A pacemaker 270 provides signals to a pump control circuit 272, which controls the actuation of the pump or pumps in a pumping mechanism 274. The pumping mechanism inflates and deflates the balloons in a heart assist device 276. The pacemaker 270 also produces heart stimulation signals. The pacemaker 270 provides signals to the pump control circuit 272 so that inflation and deflation of the balloons are timed to appropriately correspond to the heart stimulation signals that the pacemaker 270 generates. The configuration depicted in FIG. 25 may be employed if the entire device is implanted within the body of the patient. Furthermore, this configuration may be used where the pumping mechanism 274 includes a muscle pump of the type described during the discussion of FIG. 9. In this embodiment, the pacemaker 270 also outputs signals that stimulate the muscle of the muscle pump. A control relay may be used in lieu of a pacemaker, as mentioned previously.

As can be seen, the present invention provides a significant advance over the present state of technology. As numerous additions, modifications, and constructions can be performed within the scope of the invention, such scope is to be measured by the claims herein.

We claim:

1. A heart assist device, comprising:
    a catheter with a proximal end and a distal end, the catheter having a first lumen running between the proximal end and the distal end;
    a first tube with a first end and a second end, the first end of the first tube being connected to the distal end of the catheter;
    a second tube with a first end and a second end, the first end of the second tube being connected to the distal end of the catheter;
    a first inflatable intraventricular balloon, the first intraventricular balloon being connected to the first tube at the second end of the first tube, the interior of the first intraventricular balloon communicating with the first lumen through the first tube;
    a second inflatable intraventricular balloon, the second intraventricular balloon being connected to the second tube at the second end of the second tube, the interior of the second intraventricular balloon communicating with the first lumen through the second tube;
    pumping means for inflating and deflating the first intraventricular balloon and for inflating and deflating the second intraventricular balloon, the pumping means being connected to the catheter at the proximal end of the catheter.

2. A heart assist device as recited in claim 1, wherein the second intraventricular balloon is less elastic than the first intraventricular balloon.

3. A heart assist device as recited in claim 1, wherein the first intraventricular balloon contains means for weighting the first intraventricular balloon and wherein the second intraventricular balloon contains means for weighting the second intraventricular balloon.

4. A heart assist device as recited in claim 3, wherein the first intraventricular balloon contains an amount of mercury sufficient to achieve neutral buoyancy at maximal inflation of the first intraventricular balloon and wherein the second intraventricular balloon contains an amount of mercury sufficient to achieve neutral buoyancy at maximal inflation of the second intraventricular balloon.

5. A heart assist device as recited in claim 1, further comprising control means for controlling the pumping means to inflate the first and second intraventricular balloons during ventricular systole.

6. A heart assist device as recited in claim 5, wherein the control means includes means for controlling the pumping means to start inflating the first and second intraventricular balloons at the beginning of ventricular systole, to stop inflating the first and second intraventricular balloons at the end of ventricular systole, and to deflate the first and second intraventricular balloons at about the end of ventricular systole.

7. A heart assist device as recited in claim 1, further comprising an inflatable intraaortic balloon located between the proximal end of the catheter and the first intraventricular balloon, wherein the catheter has a second lumen and wherein the interior of the intraaortic balloon communicates with the second lumen.

8. A heart assist device as recited in claim 7, wherein the pumping means includes a first pump connected to the first lumen, a second pump connected to the second lumen, and control means for controlling the first pump and the second pump to inflate the first and second intraventricular balloons while the intraaortic balloon is deflating.

9. A heart assist device as recited in claim 8, wherein the control means includes means for controlling the first pump to inflate the first and second intraventricular balloons during ventricular systole and means for controlling the second pump to inflate the intraaortic balloon during ventricular diastole.

10. A method for using a heart assist device having a catheter with a proximal end and a distal end, the catheter having a lumen formed therein running between the proximal and distal ends thereof, a first inflatable intraventricular balloon connected to the distal end of the catheter and communicating with the lumen thereof, a second inflatable intraventricular balloon connected to the distal end of the catheter and communicating with the lumen thereof, and pumping means for inflating the first and second intraventricular balloons through the lumen of the catheter, comprising the steps of:
    inserting the first intraventricular balloon into the left ventricle of the heart;
    inserting the second intraventricular balloon into the right ventricle of the heart;
    inflating the first and second intraventricular balloons during ventricular systole;
    deflating the first and second intraventricular balloons during ventricular systole;
    deflating the first and second intraventricular balloons; and
    repeating the inflating and deflating steps.

11. A method as recited in claim 10, wherein the step of inflating the first and second intraventricular balloons starts at approximately the beginning of ventricular systole and stops at approximately the end of ventricular systole, and wherein the step of deflating the first and second intraventricular balloons occurs at approximately the onset of ventricular diastole.

12. A method as recited in claim 10, further comprising the steps of:
    monitoring the heart with an electrocardiograph; and
    actuating the pumping means in response to signals from the electrocardiograph.

13. A method as recited in claim 10, wherein the step of inserting the first intraventricular balloon includes inserting the first intraventricular balloon into the left ventricle through the apex of the left ventricle and wherein the step of inserting the second intraventricular balloon includes inserting the second intraventricular balloon into the right ventricle through the apex of the right ventricle.

14. A method as recited in claim 10, further comprising the step of implanting the pumping means within a patient's body.

15. A method as recited in claim 14, wherein the implanting step includes implanting the pumping means within an envelope of skeletal muscle.

16. A method as recited in claim 15, further comprising the step of stimulating the envelope of skeletal muscle to inflate the first and second intraventricular balloons.

17. A method as recited in claim 10, further comprising the steps of:
  introducing means for weighting the first intraventricular balloon into the first intraventricular balloon; and
  introducing means for weighting the second intraventricular balloon into the second intraventricular balloon.

18. A method as recited in claim 17, wherein the first introducing step includes introducing an amount of mercury sufficient to achieve neutral buoyancy at maximal inflation of the first intraventricular balloon and wherein the second introducing step includes introducing an amount of mercury sufficient to achieve neutral buoyancy at maximal inflation of the second intraventricular balloon.

19. A method for using a heart assist device having a catheter with a proximal end and a distal end, the catheter having a lumen formed therein running between the proximal and distal ends thereof, a first inflatable intraventricular balloon connected to the distal end of the catheter and communicating with the lumen thereof, a second inflatable intraventricular balloon connected to the distal end of the catheter and communicating with the lumen thereof, an intraaortic balloon located between the proximal end of the catheter and the first intraventricular balloon, and pumping means for inflating the first and second intraventricular balloons through the lumen of the catheter, and for inflating the intraaortic balloon, comprising the steps of:
  inserting the first intraventricular balloon into the left ventricle of the heart;
  inserting the second intraventricular balloon into the right ventricle of the heart;
  positioning the intraaortic balloon in the aorta;
  inflating the first and second intraventricular balloons during ventricular systole;
  deflating the intraaortic balloon during ventricular systole;
  deflating the first and second intraventricular balloons;
  inflating the intraaortic balloon during ventricular diastole; and
  repeating the inflating and deflating steps.

20. A method as recited in claim 19, wherein the step of inflating the first and second intraventricular balloons and the step of deflating the intraaortic balloon start at approximately the beginning of ventricular systole and stop at approximately the end of ventricular systole and wherein the step of inflating the intraaortic balloon starts at approximately the beginning of ventricular diastole and stops at approximately the end of ventricular diastole.

21. A method as recited in claim 19, further comprising the steps of:
  monitoring the heart with an electrocardiograph; and
  actuating the pumping means in response to signals from the electrocardiograph.

22. A method as recited in claim 19, further comprising the step of implanting the pumping means within a patient's body.

* * * * *